(12) United States Patent
Glaug et al.

(10) Patent No.: US 6,566,578 B1
(45) Date of Patent: *May 20, 2003

(54) ABSORBENT ARTICLE WITH IMPROVED FLUID ACQUISITION SYSTEM AND METHOD OF MAKING THE SAME

(75) Inventors: Frank S. Glaug, Chester Springs, PA (US); William H. Cook, Cream Ridge, NJ (US); Joan Rodgers, Brookhaven, PA (US); Ruth Levy, Collegeville, PA (US); Andrew Waksmundzki, Jackson, NJ (US)

(73) Assignee: Tyco Healthcare Retail Services AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/562,541

(22) Filed: May 2, 2000

Related U.S. Application Data

(63) Continuation-in-part of application No. 09/439,793, filed on Nov. 12, 1999.

(51) Int. Cl.[7] .................................................. A61F 13/15
(52) U.S. Cl. .................. 604/378; 604/585.01; 604/366; 604/367; 604/374; 604/379; 604/365; 428/137; 428/138
(58) Field of Search ................................. 604/379, 378, 604/385.01, 370, 365, 366; 428/137, 138

(56) References Cited

U.S. PATENT DOCUMENTS

| | | | |
|---|---|---|---|
| 3,929,135 A | 12/1975 | Thompson | 128/287 |
| 4,324,246 A | 4/1982 | Mullane et al. | 128/287 |
| 4,327,730 A | 5/1982 | Sorensen | 128/287 |
| 4,463,045 A | 7/1984 | Ahr et al. | 428/131 |
| 4,552,709 A | 11/1985 | Koger, II et al. | 264/504 |
| 4,601,868 A | 7/1986 | Radel et al. | 264/504 |
| 4,609,518 A | 9/1986 | Curro et al. | 264/504 |
| 4,629,643 A | 12/1986 | Curro et al. | 428/131 |

(List continued on next page.)

FOREIGN PATENT DOCUMENTS

| | | |
|---|---|---|
| EP | 0207904 | 1/1987 |
| EP | 0596532 | 5/1994 |
| GB | 2294901 | 5/1996 |
| WO | WO 9218078 | 10/1992 |
| WO | WO 9309744 | 5/1993 |

*Primary Examiner*—John J. Calvert
*Assistant Examiner*—Angela J Grayson
(74) *Attorney, Agent, or Firm*—Caesar, Rivise, Bernstein, Cohen & Pokotilow, Ltd.

(57) ABSTRACT

A disposable absorbent article, e.g., a diaper, and a method of making it. The article is arranged to be worn by a wearer to trap and collect fluid waste products, e.g., urine, of the wearer. The article has a flexible chassis and plural tabs for holding the diaper in place on the wearer. The chassis is made up of a top-sheet, a fluid acquisition system, and a fluid absorbent core. The top sheet is formed of a fluid pervious material, e.g., a fibrous material. The core includes fast acting fluid absorbing material, e.g., fluff, and a slow acting fluid absorbing and retaining material, e.g., SAP. The fluid acquisition system comprises a first fluid acquisition layer formed of apertured polymeric, e.g., three dimensional, film and a second fluid acquisition layer, e.g., a fibrous material, secured together and located between the top-sheet and the core, with the first fluid acquisition layer facing the top-sheet and the second fluid acquisition layer facing the core. The fluid acquisition system serves to facilitate the transference of fluid into the core, e.g., spread out the fluid over the core and providing it to the core at a rate at which the materials of the core can accommodate. The first and second acquisition layers may be joined or bonded together via various techniques, such as by adhesives, ultrasonic bonding, heat sealing, hot knife-slitting, hydroentanglement, physical stitching or sewing, etc.

36 Claims, 2 Drawing Sheets

U.S. PATENT DOCUMENTS

| | | | | |
|---|---|---|---|---|
| 4,690,679 | A | 9/1987 | Mattingly, III et al. | 604/383 |
| 4,695,278 | A | 9/1987 | Lawson | 604/385 A |
| 4,726,976 | A | 2/1988 | Karami et al. | 428/137 |
| 4,738,675 | A | 4/1988 | Buckley et al. | 604/380 |
| 4,764,234 | A | 8/1988 | Smits et al. | 156/164 |
| 4,764,242 | A | 8/1988 | Gressick et al. | 156/494 |
| 4,795,451 | A | 1/1989 | Buckley | 604/385.2 |
| 4,795,454 | A | 1/1989 | Dragoo | 604/385.2 |
| 4,804,379 | A | 2/1989 | Toth et al. | 604/378 |
| 4,806,411 | A | 2/1989 | Mattingly, III et al. | 428/139 |
| 4,900,318 | A | 2/1990 | Toth | 604/385.1 |
| 4,988,344 | A | 1/1991 | Reising et al. | 604/368 |
| 4,994,037 | A | 2/1991 | Bernardin | 604/368 |
| 5,263,948 | A | 11/1993 | Karami et al. | 604/383 |
| 5,263,949 | A | 11/1993 | Karami et al. | 604/383 |
| 5,294,478 | A | 3/1994 | Wanek et al. | 428/218 |
| 5,300,054 | A | 4/1994 | Feist et al. | 604/378 |
| 5,304,161 | A | 4/1994 | Noel et al. | 604/378 |
| 5,308,344 | A | 5/1994 | Toth | 604/378 |
| 5,387,208 | A | 2/1995 | Ashton et al. | 604/378 |
| 5,437,653 | A * | 8/1995 | Gilman et al. | 604/358 |
| 5,439,458 | A * | 8/1995 | Noel et al. | 604/358 |
| D362,120 | S | 9/1995 | Suskind et al. | D5/1 |
| 5,460,622 | A | 10/1995 | Dragoo et al. | 604/378 |
| D364,040 | S | 11/1995 | Suskind | D5/1 |
| 5,486,167 | A | 1/1996 | Dragoo et al. | 604/384 |
| 5,514,105 | A | 5/1996 | Goodman, Jr. et al. | 604/370 |
| 5,520,673 | A | 5/1996 | Yarbrough et al. | 604/378 |
| 5,522,809 | A | 6/1996 | Larsonneur | 604/361 |
| H1575 | H | 8/1996 | Daugherty et al. | 428/284 |
| 5,558,655 | A | 9/1996 | Jezzi et al. | 604/378 |
| 5,591,149 | A | 1/1997 | Cree et al. | 604/378 |
| 5,599,334 | A | 2/1997 | Johnston et al. | 604/368 |
| 5,607,414 | A | 3/1997 | Richards et al. | 604/378 |
| 5,609,588 | A | 3/1997 | DiPalma et al. | 604/369 |
| 5,730,737 | A | 3/1998 | Widlund et al. | 604/378 |
| 5,752,945 | A | 5/1998 | Mosley et al. | 604/370 |
| 5,833,678 | A | 11/1998 | Ashton et al. | 604/378 |
| 5,843,055 | A | 12/1998 | Seger | 604/365 |
| 5,855,572 | A | 1/1999 | Schmidt | 604/378 |
| 5,895,379 | A | 4/1999 | Litchholt et al. | 604/378 |
| 5,906,602 | A | 5/1999 | Weber et al. | 604/385.1 |
| 6,103,953 | A * | 8/2000 | Cree et al. | 604/365 |
| 6,316,687 | B1 * | 11/2001 | Davis et al. | 604/372 |
| 6,455,753 | B1 * | 9/2002 | Glaug et al. | 604/368 |

* cited by examiner

ABSORBENT ARTICLE WITH IMPROVED FLUID ACQUISITION SYSTEM AND METHOD OF MAKING THE SAME

RELATED APPLICATION

This application is a Continuation-In-Part of our earlier filed U.S. patent application, Ser. No. 09/439,793 filed on Nov. 12, 1999, entitled Absorbent Article with Improved Fluid Acquisition System, which is assigned to the same assignee as this invention and whose disclosure is incorporated by reference herein.

FIELD OF THE INVENTION

This invention relates generally to disposable absorbent articles and more specifically to disposable absorbent articles, e.g., diapers, which exhibit enhanced liquid absorption and trapping characteristics.

BACKGROUND OF THE INVENTION

Disposable absorbent articles, e.g., diapers, catamenial pads, panty liners, shields, etc., frequently make use of a liquid absorbent core located between a top-sheet and a back sheet. The top-sheet is commonly formed of a material which is pervious to body fluids, e.g., urine, to promote the transfer of such fluids into the core with minimal fluid retention by the top-sheet. The back-sheet is commonly formed of a liquid impervious or hydrophobic material to form a barrier wall so that any fluid absorbed by the article cannot escape out the back-sheet. In many cases, a fluid "acquisition," "surge" or "transfer" layer is located between the top-sheet and the core to facilitate the transference of body fluid(s) into the core.

In some applications the top-sheet of the disposable absorbent article is formed a woven, non-woven or carded fibrous web. In other cases a perforated or apertured polymeric film is used in place of the fibrous web top-sheet. Typically most of such apertured films are of a three dimensional nature, e.g., they are embossed and/or debossed to include numerous protuberances, channels, capillaries, hills and valleys, etc. Such three dimensional apertured film top-sheets exhibit a pleasing soft, cloth-like appearance similar to that of the prior art woven, non-woven or carded fibrous webs, while providing for a quick and efficient transfer of liquid therethrough to the underlying absorbent layer(s).

Examples of perforated three dimensional film top-sheets are found in U.S. Pat. No. 3,929,135 (Thompson), U.S. Pat. No. 4,324,246 (Mullane et al.), U.S. Pat. No. 4,327,730 (Sorensen), U.S. Pat. No. 4,463,045 (Ahr et al), U.S. Pat. No. 4,552,709 (Koger et al.), U.S. Pat. No. 4,601,868 (Radel), U.S. Pat. No. 4,609,518 (Curro et al.), U.S. Pat. No. 4,629,643 (Curro et al.), U.S. Pat. No. 4,690,679 (Mattingly, III et al.), U.S. Pat. No. 4,806,411 (Mattingly, III et al.), U.S. Pat. No. 5,514,105 (Goodman et al.), U.S. Pat. No. D362,120 (Suskind et al), and U.S. Pat. No. D364,040 (Suskind), and in U.S. Statutory Invention Registration H1575 (Daugherty et al.).

The absorbent core of many disposable diapers and other higher performance incontinence products, e.g., adult briefs, typically have cores with enhanced absorbency capability. This enhanced absorbency can be accomplished by use of an air-laid super absorbent material, or by the inclusion of absorbency enhancers, e.g., materials sometimes referred to as "super-absorbent-polymers" (which may be in the form of particles or fibers) with other absorbent materials, such as a fluff, e.g., comminuted wood pulp or other cellulosic fibers. Examples of super absorbent materials are hydrogel polymer particulates, sometimes referred to as "SAP," and hydrogel polymer fibers, sometimes referred to as "SAF." The fluff for the core serves as a means for quickly absorbing the liquid transferred to it. Unfortunately, while fluff is suitable for the task of quick absorption it is somewhat deficient from the standpoint of liquid retention and ability to accommodate repeated insults. SAP on the other hand, has the ability to retain absorbed liquid and to handle repeated insults. The drawback with SAP and SAF are their slowness in absorbing liquid. Accordingly, heretofore disposable absorbent articles have typically taken two approaches to ensure efficient action. In particular, they have included a higher ratio of SAP to fluff to facilitate the rapid absorption of the liquid by the fluff of the core until to SAP can absorb and trap it, and have also included an the heretofore mentioned acquisition or surge layer (also sometimes called a "transfer" layer) disposed over the core. Acquisition layers have typically been constructed of a woven, non-woven or carded fibrous material. They are arranged to quickly absorb the liquid through the absorbent article's cover stock, liner, or top-sheet for temporary retention (e.g., to act as a temporary reservoir), and to transfer that liquid into the underlying core at a rate at which the core can absorb for final or permanent retention. In particular, an acquisition layer improves "wicking" of the absorbent article by spreading the body fluid in the "x" and "y" plane over the area of the core encompassed by the acquisition layer while also carrying the fluid in the "z" direction to the core.

Examples of prior art acquisition layers are disclosed in U.S. Pat. No. 4,988,344 (Reising et al.), U.S. Pat. No. 4,994,037 (Bernardin), U.S. Pat. No. 5,294,478 (Wanek et al.), U.S. Pat. No. 5,300,054 (Feist et al.), U.S. Pat. No. 5,304,161 (Noel et al.), U.S. Pat. No. 5,387,208 (Ashton et al.), U.S. Pat. No. 5,460,622 (Dragoo et al.), U.S. Pat. No. 5,486,167 (Dragoo et al.), U.S. Pat. No. 5,520,673 (Yarbrough et al.), U.S. Pat. No. 5,522,809 (Larsonneur), U.S. Pat. No. 5,558,655 (Jezzi et al.), U.S. Pat. No. 5,591,149 (Cree et al.), U.S. Pat. No. 5,607,414 (Richards et al.), U.S. Pat. No. 5,609,588 (DiPalma et al.), U.S. Pat. No. 5,730,737 (Widlund et al.), U.S. Pat. No. 5,752,945 (Mosley et al.), U.S. Pat. No. 5,833,678 (Ashton et al.), U.S. Pat. No. 5,843,055 (Seger), U.S. Pat. No. 5,855,572 (Schmidt), U.S. Pat. No. 5,895,379 (Litchholt et al.), and U.S. Pat. No. 5,906,602 (Weber et al.). Examples of commercially available materials used for acquisition layers in disposable absorbent articles are through-air bond staple fibers, adhesively bonded staple fibers, and thermally point bonded staple fibers.

As will be appreciated by those skilled in the art increasing the SAP (or other absorption enhancing material) to fluff ratio to provide an absorbent product, e.g., diaper, suitable for accommodating multiple insults of body fluids would concomitantly place an additional burden on the liquid acquisition layer to facilitate transfer of the liquid at a rate that the SAP/other absorption enhancing material could accommodate. Heretofore the materials making up the prior art liquid acquisition layers have provided less than desired results.

Accordingly a need exists for a diaper or other high capacity absorbent article making use of a relatively high SAP/other absorption enhancing material content core and an effective liquid acquisition system to transfer the liquid into the core.

Various absorbent articles which are commercially available have made use of various layers of materials. For example, sanitary pads made by The Kendall Confab Retail Group and sold under the trademark EVERYDAY PANTILINER have included atop sheet formed of a fibrous material over the marginal edges of the pad, but not over the intake or "target" zone (i.e., the area at which the body fluid(s) gain(s) ingress into the absorbent article), a three dimensional apertured film forming the top layer of the intake/target zone, a fluid acquisition layer formed of a fibrous material (non-woven) web, and a core formed of an air laid web containing super absorbent material. Other pads in the form of Ultra Thins are also made by The Kendall Confab Retail Group and sold under trademark FRESH TIMES have included a top sheet formed of an apertured film, an air-laid acquisition layer and a core formed of a combination of air-laid and SAP or an air laid super absorbent material. Still other pads in the form of Contour Maxi pads are made by The Kendall Confab Retail Group and sold under the trademark FRESH TIMES have included a top sheet formed of an apertured film and a core formed fluff. Still other pads in the form of Maxi pads are made by The Kendall Confab Retail Group and sold under the trademark FRESH TIMES have included a top sheet formed of a fibrous material, a tissue fluid acquisition layer and a core formed of fluff. Diapers made by The Kendall Confab Retail Group and sold under the trademark HAPPIES have included a non-woven top sheet, a through-air-bonded (or non-woven) acquisition layer, a tissue layer, and an absorbent core made of fluff and SAP.

While all of the foregoing articles are suitable for their intended purposes, they never the less leave something to be desired from the standpoint of fluid retention capacity and fluid transfer into a high capacity core.

OBJECTS OF THE INVENTION

It is a general object of this invention to provide a disposable absorbent article, e.g., a diaper, which addresses the needs of the prior art.

It is a further object of this invention to provide a disposable absorbent article, e.g., a diaper, which has absorbent core particularly suited for accommodating multiple insults of body and an fluid acquisition or transfer system located adjacent the core for facilitating the transference of fluid into the core.

It is still a further object of this invention to provide a disposable absorbent article, a diaper, which exhibits good strike-through and re-wet properties, even through multiple insults of body fluid.

It is yet a further object of this invention to provide a disposable absorbent article, e.g., a diaper, which is comfortable, yet provides good leakage protection for the consumer.

SUMMARY OF THE INVENTION

A disposable absorbent article, e.g., a diaper, which is arranged to be worn by a person to trap and collect fluid waste products, e.g., urine. The absorbent article is suitable for accommodating multiple insults of such fluid(s) without leakage, while also exhibiting good strike-through and re-wet properties.

The absorbent article basically comprises a top-sheet, a fluid acquisition system, and an absorbent core. The top-sheet includes a portion which forms the fluid intake or target zone of the absorbent article, with that portion of the top sheet being formed of a liquid pervious, e.g., hydrophilic, material. The absorbent core is formed of a material suitable for accommodating multiple insults of the fluid waste products, e.g., comprises fluff and super absorbent materials for good fluid retention.

The fluid system comprises a first fluid acquisition layer and a second fluid acquisition layer. The first fluid acquisition layer is located below the fluid intake zone portion of the top-sheet and over the second liquid acquisition layer. The first liquid acquisition layer is formed of an apertured film, e.g., a three dimensional apertured film. The second fluid acquisition layer is formed of a fibrous, fluid pervious material, e.g., a non-woven. The second fluid acquisition layer is located over the absorbent core.

The fluid acquisition system cooperates with the core to facilitate the transference of fluid, e.g., urine, into the core for absorption and retention in the core even under repeated insults.

When the absorbent article is in the form of a diaper it also preferably includes a back-sheet formed of a fluid impervious material.

DETAILED DESCRIPTION OF THE PREFERRED EMBODIMENT

Figure 1:
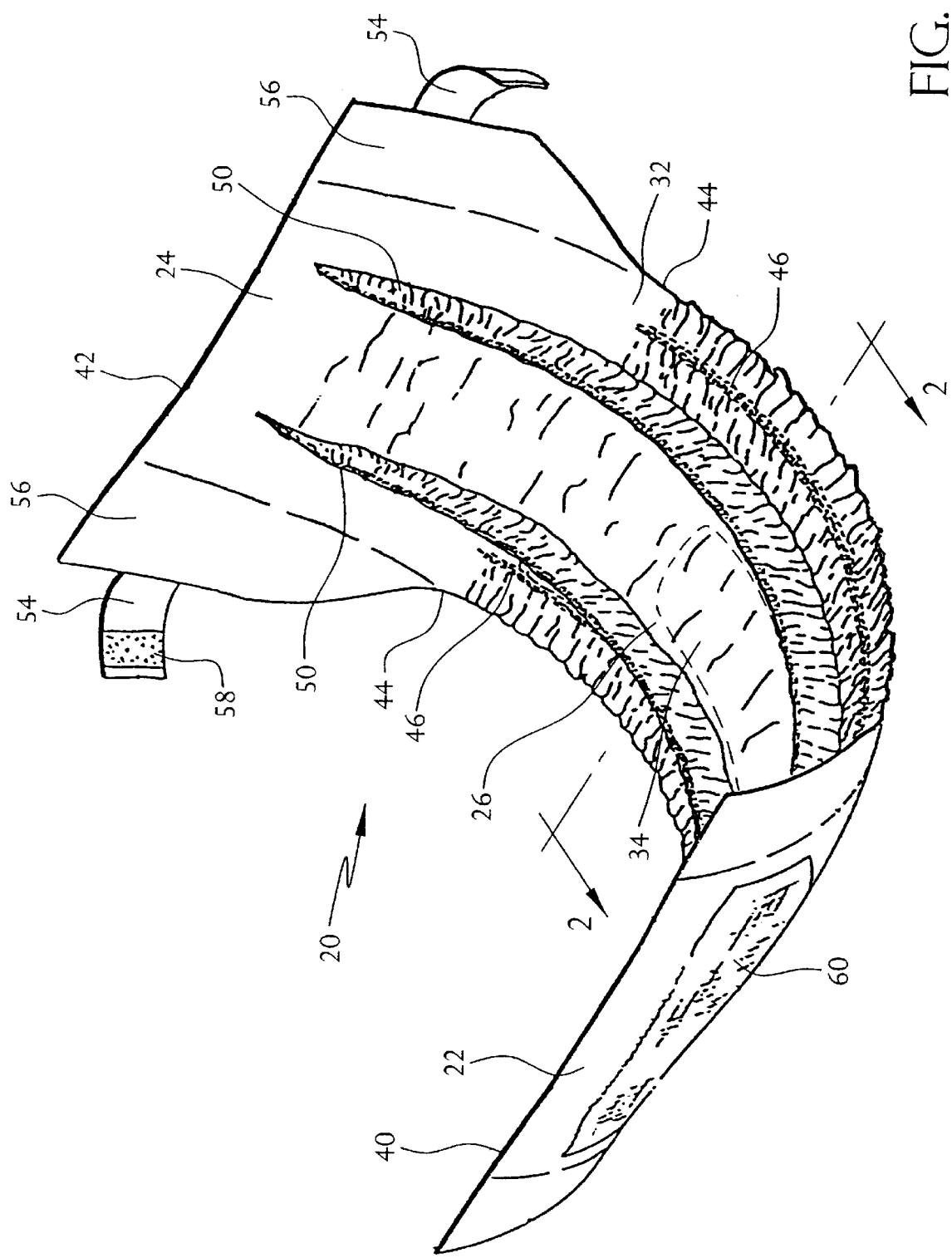
FIG. 1 is an isometric view of one preferred embodiment of the subject invention, e.g., a diaper.

Referring now to the various figures of the drawing wherein like reference characters refer to like parts, there is shown in FIG. 1 a disposable absorbent article 20 constructed in accordance with one embodiment of this invention. It should be pointed out that as used herein the term "disposable" means that article is designed to be used until soiled, either by urination or otherwise, and then discarded, rather than being washed and used again.

In the embodiment of FIG. 1 the article 20 is in the form of a diaper. While the following description will focus on diapers, it should be clear that the subject invention can be used for any type of absorbent article or garment to be worn by a person for trapping urine or menses.

Figure 2:
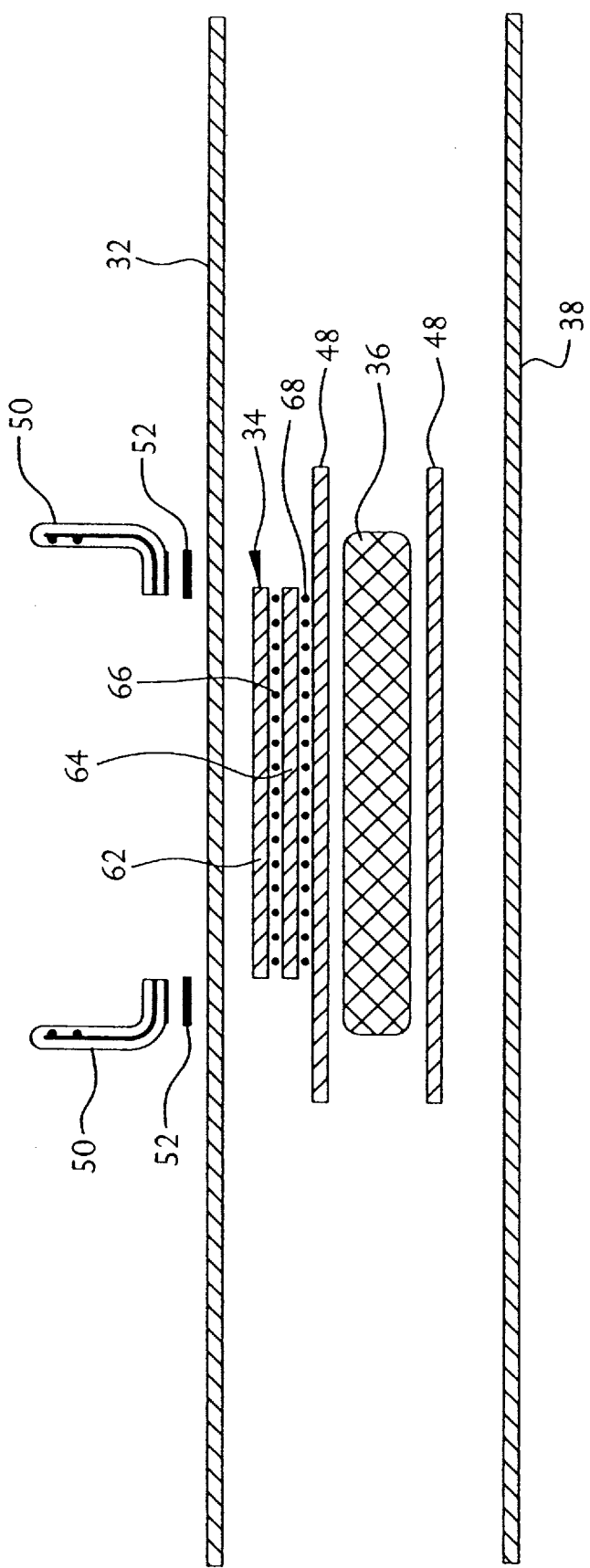
FIG. 2 is an enlarged, exploded sectional view taken along line 2—2 of FIG. 1.

The diaper 20 basically comprises a chassis including a front waist portion 22, a back waist portion 24, and a crotch portion 26 and is of generally conventional construction, except for the inclusion of fluid acquisition system for effectively transferring received body fluid(s) to an absorbent core capable of handling repeated insults of the fluid(s). In the exemplary embodiment to be described hereinafter the core includes a higher proportion of liquid-absorption-enhancing materials, e.g., SAP, in its absorbent core than commonly used in the prior art. Those components of the diaper 20 will be described in detail later. Prior to describing those components a brief description of the other portions of the diaper will now be discussed. To that end and as best seen in FIG. 2, the diaper 20 basically comprises a body-side liner or top-sheet 32, the heretofore mentioned fluid acquisition system 34 (to be described later), a liquid absorbent structure or core 36 including liquid-absorption-enhancing materials (to be described later), and an outer cover or back-sheet 38.

The top-sheet 32 is arranged to face toward the body of the user, when the diaper is in place, with the back-sheet facing away from the wearer. The top-sheet is superimposed over the back-sheet, with the absorbent core 36 interposed therebetween. The fluid-acquisition system 34 is located on top of the core and under the top-sheet to facilitate the passage of liquid waste into the core for absorption thereby. The top-sheet 32 and/or back-sheet 38 can be any suitable shape and dimensions for other designs or constructions, as will be clear from the other embodiments disclosed herein.

The back-sheet 38 comprises front edge 40, a back edge 42, and a pair of side edges 44. Each side edge includes a central, cut-out to define a respective leg cut out. The crotch portion 26 of the diaper is located between the leg cut-outs.

The top-sheet 32 may be of the same shape as the back-sheet 38 or of a different shape and is bonded to the back-sheet 36 around its entire periphery, with the absorbent material core 36 and the fluid acquisition system 34 interposed therebetween. The back-sheet and top-sheet can be joined together in any suitable manner, e.g, by adhesive bonding. The adhesives can be applied in any manner such as by spraying, slot-coat extrusion, printing, or the like. The applied adhesive can be in any desired configuration or design, such as continuous or discontinuous beads, continuous or discontinuous swirls, meltblown patterns, spray patterns, or the like. Alternatively, the joining of layers and structures can be accomplished by heat sealing, ultrasonic bonding, or the like.

Each lateral side edge 44 of the diaper 20 is elasticized by means of plural, e.g., three, longitudinally extending elastic, e.g., LYCRA 620 decitex, threads or strands 46 disposed along the length of the cut away portion of that side edge. The strands may be attained from E.I. DuPont de Nemours and Company, Wilmington, Del., and are held in place by a suitable elastic adhesive, such as that used to hold the elastic foam of the waist portion in place. The elastic adhesive is intermittently applied along the top sheet to allow the diaper to be actively stretchable along the leg cut outs and not all the way to the edges of the respective waist portions, thereby enable the diaper to closely conform about the legs of the wearer for impeding the egress of waste material from the crotch region, as is conventional. Other arrangements can be used to elasticize the sides of the crotch portion of the diaper. For example, in lieu of plural longitudinally extending elastic threads 46, multiple strands of elastic material can be arranged in other orientations, intersecting, diagonal, or any combination thereof, or can be a film or laminate of various types of elastomeric material.

The back-sheet 38 or cover is preferably formed of a laminated sheet of a non-woven material and film (with the non-woven side positioned as the outermost layer). Such material should be hydrophobic, soft in texture, and strong in tensile strength. One particularly suitable material is a spunbond-meltblown-spunbond (SMS) web having a basis weight of about 15 gms per square meter (gsm), available from AVGOL Nonwoven Industries LTD., Holon, Israel. The spunbond layer is made of polypropylene fibers. Such composites provide the dual advantages of liquid barrier properties of film along with a soft, arm outer fabric texture. The non-woven outer cover can also be made of other suitable cloth-like materials, e.g., spun-bond or thermal-bond non-woven web made of either polypropylene, polyethylene, polyester, bi-component fibers (polyethylene/polypropylene or polyethylenelpolyester), or any combinations of these fibers. Various multiple layer configurations or fiber denier variations may be used. Another example includes hydro-entangled non-woven webs, which may contain some cotton and/or rayon fibers blending in with thermal-plastic fibers. Cellulose fibers can also be blended in at small percentages to reduce cost. Still another example is a non-woven outer-cover made of stretchable or elastic materials, such as elastomeric composites of non-woven(s) and elastic membranes or a single layer of elastic material. The elastomeric composite can comprise of an inner layer of pre-stretched extruded elastic film sandwiched between and attached to a pair of non-woven webs. The non-woven webs may consist of spun-bond web, thermal-bond web, or a combination of the two. Preferably, the elastic film is made of synthetic rubber and the non-woven made of spun-bond polypropylene.

Other materials for forming the back-sheet 38 may include polypropylene films, co-extruded films (polyethylene and ethylene vinyl acetate), co-polymer films (polyethylene/polypropylene), and polylaminates (polypropylene nonwoven and polyethylene film). Still another example is a film made of a "breathable" microporous polyethylene. Suitable breathable films are available from Exxon Chemical Company, Buffalo Grove, Ill. This material allows water vapor to pass through it over time, while being impervious to liquid water. The water vapor transmission rate may range from 200–4000 grams per square meter per 24-hour period.

The fluid-acquisition system 34 will be described in considerable detail later. Suffice it for now to state that it includes at least two layers of materials which are constructed such that they cooperate to manage, transport, accommodate and/or direct high volumes and high flow rates of urine or other body fluid received from the top sheet target zone into the absorbent core 36 at a rate that the core can handle, despite multiple insults of such fluid.

In order to enable urine to quickly and efficiently pass through the top-sheet and into the underlying acquisition system 34 for subsequent transference to the absorbent core 36 for trapping therein, the top-sheet 32 is preferably liquid permeable. In particular, the top sheet may be selected from a variety of textile-like films and fabrics. Suitable fabrics include non-woven materials that are pervious to liquid, soft and pliable. Preferred non-woven materials include spun-bonded polypropylene; spun-bonded polyethylene; carded thermally bonded webs of staple fibers preferably polypropylene, polyester, polyethylene, or sheath/core bi-component fibers having a core of polyester or polypropylene and a sheath of polyethylene. Other preferred non-woven materials include through air bonded non-wovens (which comprise of sheath core bi-component fibers as discussed earlier) and adhesive bonded non-wovens made of polyester or polypropylene or polyethylene or bi-component fibers or any combination of these fibers. Still other options include fusible fiber pulp or airlaid composites, which may include cellulose fiber and/or binders in addition to thermoplastic fibers, or hydroentangled non-woven composites. To enhance the fluid control properties of the aforementioned liners, surfactants or wetting agents typified by X-100 and Triton X-102 available from Rohm & Haas Company of Philadelphia, Pa. may be applied to the fluid receiving zones of the liner selectively having the outer zones untreated to reduce migration excreted fluid such as urine into the outer diaper regions leading to diaper leakage.

If desired, the top sheet 32 may be formed of a liquid impermeable material having plural apertures or pores extending therethrough so as to make the material liquid permeable.

The absorbent core 36 is a rectangular member which is centered in the diaper and extends from close to the front waist edge to close to the back waist edge. The core can be made up of any suitable absorbent material, as well as combinations of different types of absorbent material(s). For example, in the preferred embodiment of FIG. 1 the absorbent core 36 is formed of a mixture of pulp fluff and SAP wrapped in a liquid permeable tissue wrap 48 (only two sheets of which are shown in FIG. 2). Examples of SAP include polyacrylamides, polyvinyl alcohol, polyacrylates, various grafted starches, and the like. A desired super absorbent material is a cross-linked polysodium acrylate, which can be purchased from Chemdal Corporation, Palatine, Ill., under the trademark ASAP 2260. The super absorbent materials can be in various geometric forms, such as various shaped particles, fibers, foams, and layers. The fluff and SAP are present in a ratio of about 11.5 grams of SAP to 16.5 gms of fluff for a size 4 diaper, and have a core density range of about 0.16 to 0.18 grams per cubic centimeter.

Moreover, the core 36 can be of any shape and can be a single, integral absorbent structure, or can comprise a plurality of individual separate absorbent structures and/or absorbent materials that are operably assembled together. It can also consist of air-laid non-woven web that contains super-absorbent particles and/or super-absorbent fibers, polymeric binder and cellulose pulp fibers. In one exemplary embodiment the absorbent core is sandwiched between two plies of tissue, is aligned on top of the back-sheet and adhered down with construction adhesive. The tissue has a basis weight of 17.1 gsm. Suitable tissues are available from Cellu Tissue Corporation, East Hartford, Conn. The absorbent core is centered along the transverse direction and registered in the machine (longitudinal) direction within the diaper's chassis.

The amount of each absorbent material and SAP/fluff ratio depends on the size of the brief, e.g., "Small", "Medium", "Large" or "Extra Large" and the construction of the liquid acquisition or transfer system 34.

The diaper 20 also includes a pair of conventional "standing leg gathers" or cuffs 50 or liquid-impervious gaskets to provide leakage control in the crotch region. The standing leg gathers are located so that they extend along the leg opening region of the diaper as disclosed in U.S. Pat. No. 4,695,278 (Lawson) and U.S. Pat. No. 4,795,454 (Dragoo), both of which are incorporated by reference herein. Each standing leg gather is elasticized and extends from the edge of the front waist portion to the edge of the rear waist portion and along a respective side marginal edges of the core 36 and upstanding from the top-sheet 32. The standing leg gathers are secured in place by a suitable adhesive, e.g., construction adhesive 52.

The diaper 20 is arranged to be held in place on the body of the wearer in a conventional manner, e.g., by means of a pair of fastening tabs or tapes 54 projecting outward from a pair of respective ear portions 56 forming the side edges of top sheet 32 of the diaper contiguous with its back waist portion 42. In particular, each tab 54 includes a patch 58 of a myriad of small hooks on its underside surface. Each patch is arranged to be releasably secured to a "landing zone" portion 60 on the outer cover in the front waist region of the diaper. The landing zone is located at a position so that when the diaper is folded in half with the front waist portion disposed opposite the back waist portion, the landing zone 60 will be aligned with the tabs 54.

The landing zone 60 basically comprises a rectangular panel of whose outer surface comprises a myriad of small loops arranged to be engaged by the small hooks of the patch 58 of each fastening tab.

When the diaper is in place on the person with the front waist portion disposed over the lower abdomen, the back waist portion disposed over the lower back and buttocks region, and the crotch portion between the legs, each tab 54 may be brought into engagement with the a portion of the landing zone 60 closest to that tab on the front portion of the diaper so that the myriad of hooks on the patch engage the myriad of loops of the landing zone 60 to releasably secure the tab thereto. Any suitable multi-hook and multi-loop materials may be used. Particularly suitable multi-hook patches 54 are available from 3M Corporation, St. Paul, Minn., under the model designation CS-1010 hook, while a particularly suitable multiloop material is an extruded bonded laminate material also available from 3M Corporation under the model designation EBL, and which contains a polypropylene non-woven having a basis weight of 53 grams per square meter with a laminated polypropylene film (1.0 mil) backing.

Alternatively the tabs 54 may be in the form of adhesive tapes, such as those available from 3M Corporation, St. Paul, Minn., and the landing zone may be formed of a polyester film with a pre-applied adhesive in a selected print pattern, such as also available from 3M Corporation, St. Paul, Minn.

As mentioned earlier, the fluid-acquisition system basically comprises at least two layers disposed over each other. In particular, the uppermost of the layers making up the fluid acquisition system 34 comprises an apertured polymeric film 62, which is preferably three dimensional in nature, e.g., is embossed and/or debossed, like that used heretofore and described above for cover sheets of diapers. One particularly suitable material is available from Tredegar Film Products of Terra Haute, Ind. under the trade designation C120 and basically comprises a polyethylene film apertured like that shown in U.S. Pat. No. D362,120 (Suskind et al.), whose disclosure is incorporated by reference herein. Other three dimensional polymeric apertured films, such as those in the patents discussed above, can be utilized to form the first fluid acquisition layer 62. In fact, for some applications two dimensional apertured films, like those of the prior art, may be used for the layer 62.

The lowermost layer making up the fluid acquisition system 34 is designated by the reference number 64 and can be any type of fibrous material, e.g., a through-air bonded/carded web with bi-component fibers, a spun-bond non-woven web, a web of cross-linked cellulosic fibers, an adhesive bonded non-woven web, a carded thermal bonded non-woven web, a hydroentangled non-woven web, an airlaid composite web, a spunbond-meltblown-spunbond non-woven web, or any combination thereof. One particular suitable material is available from PGI Nonwovens, Landisville, N.J., and has an overall basis weight of 40 gsm, with high denier (10 denier) bi-component fibers situated on the top (facing the top-sheet) and low denier (6 denier) bi-component fibers situated on the bottom (facing the core 36). The bi-component fibers are made of a polypropylene inner core and polyethylene outer sheath.

The uppermost and lowermost layers are preferably, but not mandatorily, adhered or secured together by any suitable adhesive 60 (e.g., a construction adhesive or hydrophillic adhesive, such as Cycloflex adhesive available from National Starch and Chemical, Bridgewater, N.J. The upper most and lowermost layers can also be joined or bonded together by various other methods, such as ultrasonic bonding, heat sealing, hot knife slitting, hydroentanglement, physical stitching or sewing, etc., or any other suitable technique known in the art.

The fluid-acquisition system 34 is also preferably adhesively secured in place by any suitable adhesive 60 (e.g., a construction adhesive or hydrophillic adhesive, such as Cycloflex adhesive available from National Starch and Chemical, Bridgewater, N.J.). In the exemplary embodiment described above, 16.5 grams of fluff and 11.5 grams of SAP is used for the absorbent core for both the "Medium" and "Large" sizes of diapers, with a transfer or acquisition system including an upper layer 62 of 26.3 gsm, and a lower layer 64, of 20 gsm/70 mm through air bonded bicomponent fibers adhered on top of the absorbent core in a "continuous" configuration. A higher basis weight acquisition layer 64, e.g., 50 gsm/70 mm thermal bonded polypropylene fibers, with a variety of fiber material combinations and deniers, can be also used. The lower layer 64 may be in the range of 10–50 gsm/20–230 mm through air bonded bicomponent fibers. Other high-absorbency materials can also be used for the core, such as super absorbent fibers or peat moss.

The acquisition system 34 can be secured in place by either adhesively securing its upper layer 62 to the top sheet 32 and/or by adhesively securing it lower layer 64 to the core 36. In the exemplary embodiment shown herein the lower layer 64 is secured to the tissue covering 48 of the core.

If desired the core 36 may be held in place by a hydrophillic construction adhesive, 5 such as Cycloflex from National Starch and Chemical Corporation, Bridgewater, N.J. In such an arrangement the adhesive may be applied on undersurface of the lower layer 64 of the acquisition system as well as the inner surface of the back sheet 36.

In order to facilitate the transference of the body fluid(s) through the absorbent article into the core 36, one or more of the various layers may be treated with any suitable surfactant(s), such as a "fast finish" surfactant for the layer 64 and monoglyceride and diglyceride for the layer 62. In the exemplary embodiment the layer 62 treated with a suitable surfactant is available from Tredegar Film Products of Terra Haute, Ind. as X-6958 white C120 apertured film. It should be pointed out at this juncture that in the exemplary embodiment of the diaper shown and described herein both the layers 62 and 64 are treated with surfactants, but either or neither layer may be so treated.

As best seen in FIG. 1 the acquisition system 34 is located in the diaper over the core in the front portion of the diaper making up the fluid intake or target zone of the diaper, i.e., the portion of the diaper to directly receive the liquid body waste(s) from the wearer. If desired the acquisition system 34 can be extended into the rear portion of the diaper, as well.

The absorbent article 20 operates as follows upon the receipt of a fluid (e.g., urine) insult to its top sheet 32 intake zone. The fluid penetrates the top sheet 32 and passes through the apertured polymeric layer (film) 62 of the fluid acquisition system generally perpendicularly to the layer 62. Fluid flow is faster into the diaper 20, i.e., through the top sheet into the diaper, than coming out of the diaper through the top sheet. This is due to the fact that the apertured polymeric film 62 of the exemplary preferred embodiment has three dimensionally shaped apertures directed inwardly towards the core 36. In particular, with the preferred exemplary embodiment the apertured film 62 includes a myriad of very tiny conically shaped apertures, which taper in the direction from the top sheet 32 towards the core 36. This arrangement results in a faster and higher fluid volume intake into the diaper and a slower and lower fluid volume output after the diaper has been saturated with fluid and exposed to compressive forces. The fluid then contacts the lowermost layer 64 of the fluid acquisition system 34, where the fluid experiences some lateral distribution both transversely and longitudinally in the plane making up the layer 64 due to the fiber orientation of that layer in the machine direction. From there the fluid enters into the core for ultimate absorption and retention.

As should be appreciated by those skilled in the art from the foregoing the fluid acquisition system 34 of this invention optimizes the fluid penetration rate and volume into the absorbent core 36 below it, while also minimizing the fluid from exiting the diaper 20 when it is saturated and under high stress. The result is a diaper which exhibits high fluid intake and low fluid rewet characteristics, features which are desirable to obtain high absorbency performance with minimal fluid exposure to the wearer's skin.

Without further elaboration the foregoing will so fully illustrate our invention that others may, by applying current or future knowledge, adopt the same for use under various conditions of service.

We claim:

1. A disposable absorbent article arranged to be worn by a wearer to trap and collect fluid waste products of the wearer, said article being suitable accommodating multiple insults of said fluid waste products, said article comprising a top-sheet, a fluid acquisition system, and a fluid absorbent core, said top sheet having a portion forming a fluid intake zone, said top sheet portion being formed of a fluid pervious material, said fluid acquisition system comprising a first fluid acquisition layer and a second fluid acquisition layer, said first fluid acquisition layer comprising an apertured film, said second fluid acquisition layer comprising a fibrous, fluid pervious material, said absorbent core comprising a fluid absorbing material suitable for accommodating multiple insults of the fluid waste product, said first acquisition layer being coextensive in size and substantially coextensive in area with said second acquisition layer and located over said second acquisition layer and under said fluid intake zone of top-sheet, said second acquisition layer being located under said first acquisition layer and over said absorbent core and being secured to said first acquisition layer by one of the group consisting of adhesives, ultrasonic bonding, heat sealing, hot knife slitting, hydroentanglement and physical stitching, said first acquisition layer having a plurality of small apertures tapering in a direction toward said core.

2. The disposable absorbent article of claim 1 additionally comprising a back-sheet formed of a fluid impervious material.

3. The disposable absorbent article of claim 1 wherein said top sheet is a fibrous material.

4. The disposable absorbent article of claim 1 wherein said fluid absorbent core comprises cellulosic fibers.

5. The disposable absorbent article of claim 1 wherein said fluid absorbent core additionally comprises absorption enhancing materials.

6. The disposable absorbent article of claim 5 wherein said absorption enhancing materials comprise a super absorbent polymer.

7. The disposable absorbent article of claim 6 wherein said super absorbent polymer is a particulate.

8. The disposable absorbent article of claim 6 wherein said super absorbent polymer is fibrous.

9. The disposable absorbent article of claim 7 wherein said cellulosic fibers and super absorbent particles are comingled.

10. The disposable absorbent article of claim 8 wherein said cellulosic fibers and super absorbent fibers are comingled.

11. The disposable absorbent article of claim 1 wherein said first acquisition layer is a three-dimensional apertured film.

12. The disposable absorbent article of claim 1 wherein said first acquisition layer is adhered to said second acquisition layer.

13. The disposable absorbent article of claim 1 wherein said first acquisition layer is adhered to said top sheet.

14. The disposable absorbent article of claim 6 wherein the ratio of said super absorbent polymer to said cellulosic fibers is at least 10%.

15. The disposable absorbent article of claim 1 wherein said top sheet is formed of a fibrous material.

16. The disposable absorbent article of claim 15 wherein said fibrous material is a non-woven web.

17. The disposable absorbent article of claim 16 wherein said fibrous material is selected from the group consisting of polypropylene, polyester, polyethylene, nylon, rayon, cotton, and blends and/or bicomponent fibers thereof.

18. The disposable absorbent article of claim 16 wherein said fibrous material is selected from the group consisting of a through-air-bonded staple fiber, an adhesively-bonded staple fiber, and a thermally-point-bonded staple fiber.

19. The disposable absorbent article of claim 1 wherein said second acquisition layer is formed of a fibrous material.

20. The disposable absorbent article of claim 19 wherein said fibrous material is a non-woven web.

21. The disposable absorbent article of claim 20 wherein said fibrous material is selected from the group consisting of polypropylene, polyester, polyethylene, nylon, rayon, cotton, and blends and/or bicomponent fibers thereof.

22. The disposable absorbent article of claim 19 wherein said fibrous material is selected from the group consisting of a through-air-bonded staple fiber, an adhesively-bonded staple fiber, and a thermally-point-bonded staple fiber.

23. The disposable absorbent article of claim 1 wherein said apertured film is treated with a surfactant.

24. The disposable absorbent article of claim 1 wherein said article comprises a diaper.

25. A disposable absorbent article arranged to be worn by a wearer to trap and collect fluid waste products of the wearer, said article being suitable accommodating multiple insults of said fluid waste products, said article comprising a top-sheet, a fluid acquisition system, and a fluid absorbent core, said top sheet having a portion forming a fluid intake zone, said top sheet portion being formed of a fluid pervious material, said fluid acquisition system comprising a first fluid acquisition layer and a second fluid acquisition layer, said first fluid acquisition layer comprising an apertured film, said second fluid acquisition layer comprising a fibrous, fluid pervious material, said absorbent core comprising a fluid absorbing material suitable for accommodating multiple insults of the fluid waste product, said first acquisition layer being coextensive in size and substantially coextensive in area with said second acquisition layer and located over said second acquisition layer and under said fluid intake zone of top-sheet, said second acquisition layer being located under said first acquisition layer and over said absorbent core, said first and second acquisition layers being bonded together, said first acquisition layer having a plurality of small apertures tapering in a direction toward said core.

26. The disposable absorbent article of claim 25 wherein said first acquisition layer is ultrasonically bonded to said second acquisition layer.

27. The disposable absorbent article of claim 25 wherein said first acquisition layer is heat sealed to said second acquisition layer.

28. The disposable absorbent article of claim 25 wherein said first acquisition layer is hot knife-slit to said second acquisition layer.

29. The disposable absorbent article of claim 25 wherein said first acquisition layer is hydroentangled to said second acquisition layer.

30. The disposable absorbent article of claim 25 wherein said first acquisition layer is stitched or sewn to said second acquisition layer.

31. A method of making a disposable absorbent article arranged to be worn by a wearer to trap and collect fluid waste products of the wearer, said article being suitable accommodating multiple insults of said fluid waste products, said method comprising the steps of:

(A) providing a top-sheet, a fluid acquisition system, and a fluid absorbent core, said top sheet having a portion forming a fluid intake zone, said top sheet portion being formed of a fluid pervious material, said fluid acquisition system comprising a first fluid acquisition layer and a second fluid acquisition layer, said first fluid acquisition layer being coextensive in size and substantially coextensive in area with said second fluid acquisition layer and comprising an apertured film having a plurality of small tapering apertures, said second fluid acquisition layer comprising a fibrous, fluid pervious material, said absorbent core comprising a fluid absorbing material suitable for accommodating multiple insults of said fluid waste product;

(B) locating said first acquisition layer over said second acquisition layer and under said fluid intake zone of top-sheet, with said second acquisition layer being located under said first acquisition layer and over said absorbent core, and with said apertures tapering towards said core; and (C) bonding said first and second acquisition layers together.

32. The method of claim 31 wherein said first acquisition layer is ultrasonically bonded to said second acquisition layer.

33. The method of claim 31 wherein said first acquisition layer is heat sealed to said second acquisition layer.

34. The method of claim 31 wherein said first acquisition layer is hot knife-slit to said second acquisition layer.

35. The method of claim 31 wherein said first acquisition layer is hydroentangled to said second acquisition layer.

36. The method of claim 31 wherein said first acquisition layer is stitched or sewn to said second acquisition layer.

* * * * *